(12) United States Patent
Kutzner et al.

(10) Patent No.: US 10,327,874 B2
(45) Date of Patent: Jun. 25, 2019

(54) SUPPORT BODY FOR A BLANK

(71) Applicant: DENTSPLY International Inc., York, PA (US)

(72) Inventors: Martin Kutzner, Neuberg (DE); Stefan Fecher, Johannesberg (DE); Lothar Völkl, Goldbach (DE)

(73) Assignee: DENTSPLY SIRONA Inc., York, PA (US)

( * ) Notice: Subject to any disclaimer, the term of this patent is extended or adjusted under 35 U.S.C. 154(b) by 100 days.

(21) Appl. No.: 15/000,385

(22) Filed: Jan. 19, 2016

(65) Prior Publication Data
US 2016/0206411 A1   Jul. 21, 2016

(30) Foreign Application Priority Data
Jan. 19, 2015   (DE) .................. 10 2015 100 666

(51) Int. Cl.
  *A61C 13/00* (2006.01)
  *A61C 13/083* (2006.01)
  *B23Q 3/02* (2006.01)

(52) U.S. Cl.
  CPC ........ *A61C 13/0022* (2013.01); *A61C 13/083* (2013.01); *B23Q 3/02* (2013.01)

(58) Field of Classification Search
  CPC ....... A61C 13/002; A61C 13/083; A61C 5/77; B23Q 3/02; B24B 37/32
  USPC ...................................................... 269/287
  See application file for complete search history.

(56) References Cited

U.S. PATENT DOCUMENTS

| | | | | |
|---|---|---|---|---|
| 3,276,122 A | * | 10/1966 | Slayton | A61C 13/12 269/909 |
| 3,601,895 A | * | 8/1971 | Zollner | A61C 13/0003 433/218 |
| 3,762,032 A | * | 10/1973 | Bowling | B23K 20/02 219/160 |
| 4,644,639 A | * | 2/1987 | Atteberry | H01L 21/67132 156/229 |

(Continued)

FOREIGN PATENT DOCUMENTS

| | | |
|---|---|---|
| DE | 102005008004 A1 | 11/2005 |
| DE | 202013103515 U1 | 9/2013 |

(Continued)

OTHER PUBLICATIONS

International Search Report, PCT/EP2016/053431, May 10, 2016 (completed), dated May 20, 2016 (mailed).

(Continued)

*Primary Examiner* — Joseph J Hail
*Assistant Examiner* — Arman Milanian
(74) *Attorney, Agent, or Firm* — Dentsply Sirona Inc.

(57) ABSTRACT

The invention relates to a support body for a blank, whereby the support body possesses a receiving opening for the blank that is surrounded by an inner circumferential surface, which terminates in an upper and a lower edge, and whereby a blank fixed in position within the support body is bonded to the latter by means of an adhesive agent. In order to be able to easily introduce the adhesive agent into a gap between the blank and the support body it is intended that the inner circumferential surface possesses at least one depression and/or elevation extending to accommodate the adhesive agent.

15 Claims, 2 Drawing Sheets

(56) References Cited

U.S. PATENT DOCUMENTS

| | | | | |
|---|---|---|---|---|
| 5,791,035 | A * | 8/1998 | Yamashita | G01L 9/0051 269/287 |
| 5,813,859 | A * | 9/1998 | Hajjar | A61C 13/0003 29/896.1 |
| 6,267,655 | B1 * | 7/2001 | Weldon | B24B 37/32 451/307 |
| 7,101,180 | B2 * | 9/2006 | Filser | A61C 13/0003 433/60 |
| 7,114,891 | B2 | 10/2006 | Haakansson | |
| 7,234,938 | B2 * | 6/2007 | Bodenmiller | A61C 13/0004 29/33 R |
| 7,604,759 | B2 * | 10/2009 | Gubler | A61C 13/0004 264/16 |
| 7,789,601 | B2 * | 9/2010 | Prince | A61C 13/0022 269/287 |
| 2002/0125619 | A1 | 9/2002 | Bodenmiller | |
| 2006/0257824 | A1 * | 11/2006 | Pfeiffer | A61C 13/0004 433/218 |
| 2006/0292527 | A1 * | 12/2006 | Basler | A61C 13/0003 433/213 |
| 2007/0237595 | A1 * | 10/2007 | Steger | A61C 13/0009 409/132 |
| 2009/0023112 | A1 * | 1/2009 | Ganley | A61C 13/0022 433/215 |
| 2009/0274994 | A1 * | 11/2009 | Jung | A61C 13/0022 433/202.1 |
| 2010/0327508 | A1 * | 12/2010 | Kim | H01L 21/67069 269/287 |
| 2011/0018184 | A1 * | 1/2011 | Steger | A61C 13/0004 269/57 |
| 2011/0268525 | A1 * | 11/2011 | Karpowitz | A61C 13/0022 409/225 |
| 2012/0064300 | A1 * | 3/2012 | Huber | B28D 5/0076 428/167 |
| 2014/0087327 | A1 * | 3/2014 | Noack | A61C 13/0022 433/50 |
| 2016/0206410 | A1 * | 7/2016 | Steger | A61C 13/0004 |
| 2016/0206411 | A1 | 7/2016 | Kutzner | |
| 2017/0065381 | A1 * | 3/2017 | Schuetz | A61C 13/0022 |

FOREIGN PATENT DOCUMENTS

| | | | | |
|---|---|---|---|---|
| DE | 102012215906 A1 * | 3/2014 | | H02K 1/17 |
| DE | 102015100666 A1 | 7/2016 | | |
| KR | 101325478 B1 * | 11/2013 | | |
| WO | WO 9530382 A1 * | 11/1995 | | A61C 13/0003 |
| WO | W0200245614 A1 | 6/2002 | | |
| WO | 2014200226 A1 | 12/2014 | | |

OTHER PUBLICATIONS

European Search Report, Application Serial # 16151778.4, Jun. 13, 2016 (completed), dated Jun. 29, 2016 (mailed).

* cited by examiner

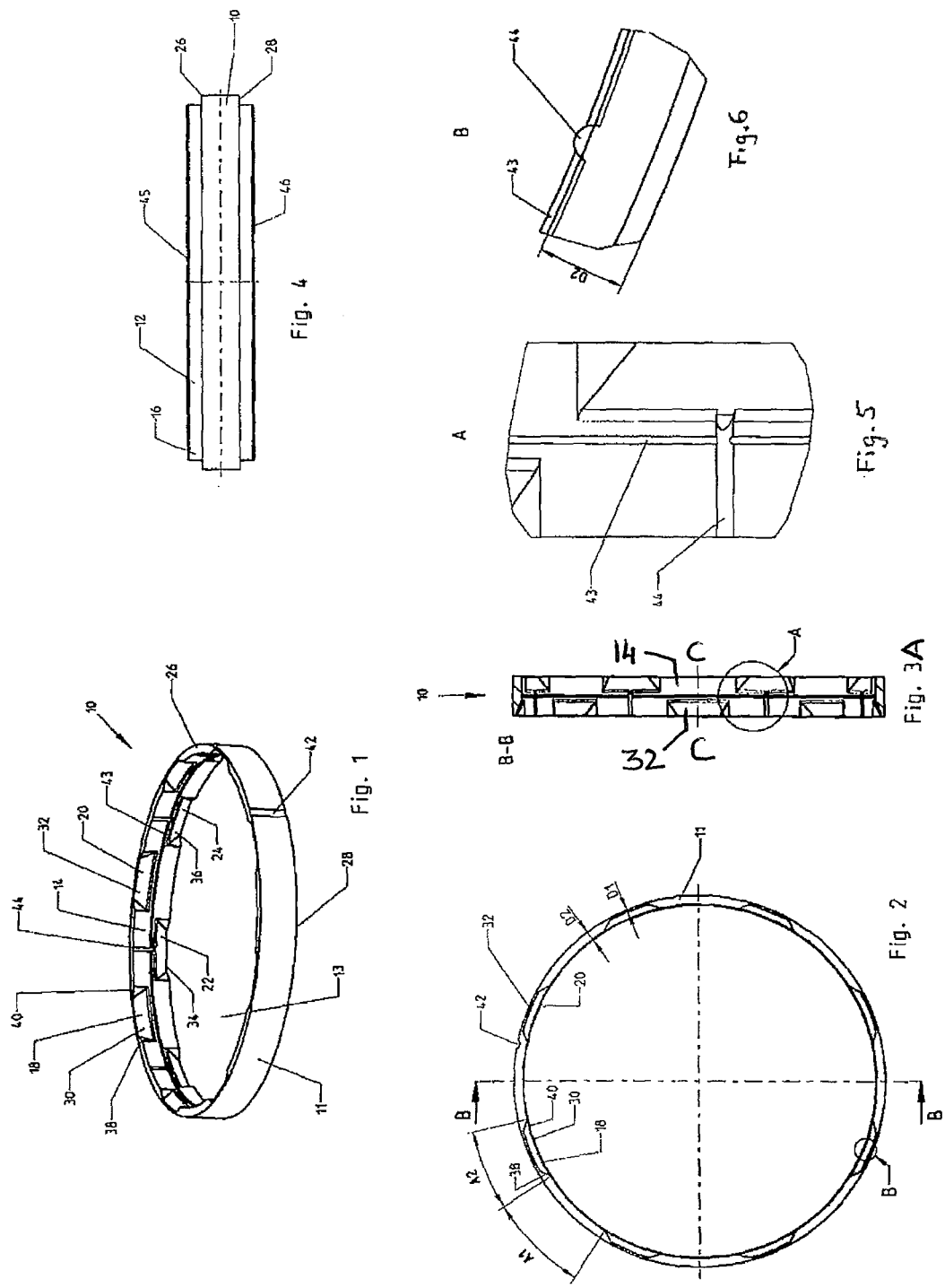

SUPPORT BODY FOR A BLANK

CROSS-REFERENCE TO RELATED APPLICATIONS

This patent application claims the benefit of and priority to German Application Ser. No. 102015100666.9, filed on Jan. 19, 2015, which is herein incorporated by reference for all purposes.

FIELD OF THE INVENTION

The invention relates to a support body for a blank, in particular a blank consisting of ceramic, such as zirconium oxide or a glass ceramic, whereby the support body possesses a receiving opening for the blank with an inner circumferential surface that terminates in an upper and a lower edge, and and whereby when the blank is fixed in the support body, the blank is bonded to the support body by means of a binding agent. In particular, the support body is embodied with a hollow-cylinder geometry. The support body circumferentially surrounds the blank, which in particular possesses a disk shape or cylinder shape.

BACKGROUND OF THE INVENTION

WO 02/45614 A1 discloses a mounting device for a ceramic blank that comprises a rectangular holder, which in turn accepts a rectangular frame, in which a blank is fixed in position by means of gluing. A two-component adhesive, for example, is introduced into an adhesive gap that exists between the blank and the frame.

In accordance with EP 0 982 009 A2, a blank is inserted into a passage opening of a plate-shaped support body.

A holding arrangement for workpieces according to WO 2007/143765 comprises a frame, in which a holder arrangement, which can accommodate a work piece by friction lock, is fixed in position by clamping.

A blank mount for a dental milling machine in accordance with DE 20 2013 103 515 U1 comprises a ring-shaped work-piece holder with clamping holders that are used to fix the blank in position.

In accordance with DE 20 2010 001 125 U1, detachable fastening elements are used to mount a blank in a mounting fixture.

For mounting a blank in a holder in accordance with DE 20 2012 008 015 U1, fastening means are provided that reach over and/or under the blank.

In accordance with DE 10 2007 013 675 A1, a UV curing adhesive is used to mount a blank in a support body, which at least partially consists of a material that is transparent at least in the UV region of the spectrum.

In accordance with DE 10 2012 201 744 A1, a molded body is fixed in position in a workpiece holder by means of fasteners, whereupon the molded body is machined in a dental milling machine.

Known from DE 10 2005 008 004 A1 is a processing method for a workpiece that is fixed in position within a tenter by means of cast resin.

During the manufacture of a dental prosthesis, in accordance with WO 95/30382 A1, a blank is embedded in a ring, which is clamped in the chuck of a processing machine.

A silicon block to be worked is connected firmly to a support. To allow the support to be reliably bonded to the silicon block, the support is provided with a profile pattern (DE 10 2009 023 122 A1).

Holders of this type are required to be able to clamp a blank in a processing machine with great positional accuracy. In this, it must not only be ensured that the holder retains its shape during clamping but also that the blank with respect to the support body assumes a unique position that cannot change during the processing.

The objective of the present invention is to further develop a support body of the above-mentioned type, in particular for accepting a blank consisting of ceramic, such as zirconium oxide, which is to be processed in a milling machine, for example, in such a way that with simple constructive measures, a secure positional fix will become possible using an adhesive agent, which can be introduced easily in between the support body and the blank and can remain between the support body and the blank to the required extent until curing has taken place.

SUMMARY OF THE INVENTION

It is an object of the present invention to at least partially overcome this problem, and to provide a medical device, such as an implant, having a surface, which reduces the risk for infection upon contact of the medical device with living tissue.

According to one aspect, the present invention is directed to a support body for a blank, in particular a blank consisting of ceramic such as zirconium oxide or a glass ceramic, whereby the support body comprises a receiving opening for the blank that is surrounded by an inner circumferential surface bordered by an upper and a lower edge and when the blank is fixed in position within the support body, it is bonded to the latter by means of an adhesive agent, whereby the support body in particular possesses a hollow cylindrical geometry and circumferentially surrounds the blank, which in turn preferably possesses a disk-shaped or cylindrical geometry, wherein the inner circumferential surface possesses a structure in form of at least one depression that extends to at least one edge and/or at least one elevation to accommodate the adhesive agent.

In another aspect, any of the aspects of the present invention may be further characterized by one or any combination of the following features: wherein the structure is formed by at least one, in particular by several preferably pocket-shaped depressions within the wall of the support body that is bordered by the inner circumferential surface, whereby the depressions extend to the at least one edge; wherein from the receiving-side area of both the upper and the lower edge originate depressions, which preferably terminate at some distance from the center of the inner circumferential surface—relative to the latter's height; wherein the depression is bordered by a first surface extending along the interior circumferential surface and lateral surfaces extending perpendicularly thereto, and in that the distance from the first surface to the central axis of the support body decreases from one edge along the direction towards the opposite edge; wherein the depressions are uniformly distributed along the inner circumference of the support body; wherein the depressions originating from one edge will exhibit the same distances to a reference mark of the support body as the depressions originating from the other edge after a rotation of the support body by 180° about its transverse axis; wherein the structure is formed in a supplementary or alternative manner by at least one elevation such as ridge and/or depression that extends at some distance to the edge and originates from the inner circumferential surface of the wall, whereby preferably the elevation and/or depression extending at some distance to the edge is provided in addition to the at least one preferably pocket-shaped depression; wherein from the inner circumferential surface originate one or several projections, such as ridges that at least in sections extend above the height of the inner circumferential surface and serve as support for the blank; wherein the first surface of the depression encloses with the inner circumferential surface an angle $\alpha$ with $20°\leq\alpha\leq30°$, in particular $\alpha=25°$; wherein in the central area of the inner circumferential surface extends a preferably circumferential ridge or depression, such as a groove, which in particular extends in parallel to the edges; wherein in the area of the depression, the wall of the support body in the edge area possesses a thickness D1 and outside of the depressions it possesses a thickness D2, whereby $8*D1\geq D2\geq2*D1$; wherein the distance A1 between successive depressions relative to the length A2 of the respective depression along the circumferential direction obeys $A2\leq A1\leq2*A2$; wherein the support body consists of plastic, in particular of fiber reinforced plastic such as glass fiber reinforced plastic such as thermoplastic, whereby in particular the thermal expansion coefficient $WAK_H$ of the material is matched to the thermal expansion coefficient $WAK_R$ of the blank, and in particular the thermal expansion coefficients differ no more than 20%, preferably no more than 10%; wherein the fiber content such as glass fiber content of the support body amounts to between 30% by volume and 70% by volume, in particular approximately 50% by volume; or any combination thereof.

BRIEF DESCRIPTION OF THE DRAWINGS

FIG. 1 shows a perspective representation of a support body,

FIG. 2 shows a top view onto the support body of FIG. 1,

FIG. 3A shows a sectional view along the line B-B of FIG. 2,

FIG. 4 shows the support body of FIGS. 1 to 3A together with a blank, FIG. 5 shows a detail "A" of FIG. 3A, FIG. 6 shows a detail "B" of FIG. 2.

DETAILED DESCRIPTION OF THE INVENTION

Figure 3B:
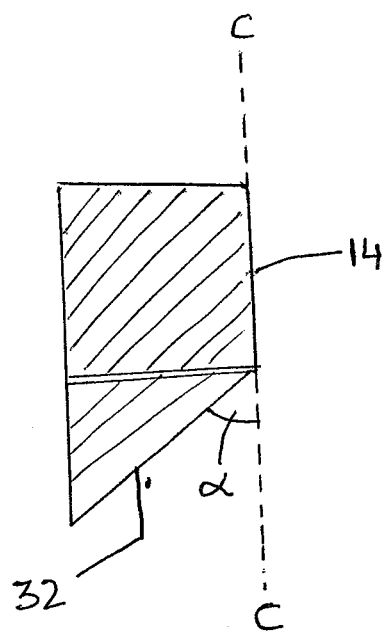
FIG. 3B shows a cross-sectional view along the line C-C of FIG. 3A.

In the present invention, this objective is substantially met that the inner circumferential surface possesses a structure that is formed by at least one depression that extends to at least one edge of the inner circumferential surface and/or at least one elevation that protrudes from the inner circumferential surface for the acceptance of an adhesive agent.

In accordance with the invention, the structural pattern of the inner surface, i.e. the formation of at least one depression and/or one elevation, makes it possible to introduce an adhesive agent into the space between the blank and the support body to the required extent, which remains in the gap sufficiently long for curing to take place.

In particular, it is intended that the structure is formed by at least one, in particular by several preferably bag-shaped depressions in the wall of the support body that is bordered by the inner circumferential surface, which extends or extend to the at least one edge, i.e. originates or originate from the edge.

This to be emphasized embodiment of the structure ensures that—independently of a small distance between the blank and the inner circumferential surface of the support body—adhesive agent can be introduced to an adequate degree, in particular via the pocket-shaped depression or depressions. The depressions are arranged at some distance from each other so that the wall thickness of the support body, which preferably possesses a ring-shaped or hollow-cylindrical geometry, remains constant over large areas, which ensures the required amount of stability to ensure that the support body does not deform during the clamping process.

In particular it is intended that depressions originate in the receiving-side areas of both the upper and the lower edge and preferably end at some respective distance to the center—with respect to its height—of the inner circumferential surface.

In a top view onto the support body, the depressions originating from the lower or upper edge are arranged offset with respect to each other, so that there is no weakening of the wall of the support body between the inner boundary of a depression and the opposite edge.

In order to be able to introduce the adhesive agent easily and at the same time to weaken the wall as little as possible, a further development intends that the depression is bordered by a first surface that extends along the inner circumferential surface and a lateral surface extending perpendicular thereto, and that the distance of the first surface to the central axis of the support body decreases from its origin at one edge along the direction towards the opposite edge.

The first surface, which extends along the circumferential surface and also extends into the latter consequently possesses a ramp shape and consequently extends inclined with respect to the longitudinal axis of the support body. The first surface is bordered by lateral surfaces, which do not necessarily have to extend in parallel, but in a sectional view can exhibit a trapezoidal geometry together with the first surface. Thus the edges of the first surface may have the shape of a trapeze.

In order to offer enough free space to introduce the adhesive agent, even if there is only a narrow gap between the blank and the inner circumferential surface, it is intended that in the area of the depressions, the wall of the support body in the edge area has a thickness D1 and that the wall outside of the depressions has a wall thickness D2, with $8*D1\geq D2\geq2*D1$. D2 may for example be 1.5 mm to 5 mm, in particular D2=2.5 mm.

In a preferred manner the invention intends that the distance A1 between successive depressions relative to the length A2 of the respective depression in the circumferential direction obeys $A2\leq A1\leq2*A2$. The distances A1 and A2 may be specified as arc length if the support body possesses a circular geometry. In this case, the central angle between two consecutive depressions should be between 20° and 30°, with a preferred value of 25°. The central angle for the length of the depression should be between 15° and 25°, in particular 20°.

During the introduction of the adhesive agent, the support body, which as mentioned above preferably possesses a ring-shaped or hollow-cylindrical geometry with edges extending in parallel to each other, is fixed in position, such as clamped, in order to subsequently fill the individual depressions, i.e. pockets, with an adhesive agent. Since preferably pocket-shaped depressions originate from each of the edges, a suggestion to be emphasized intends that the depressions originating from one edge have the same distance from a reference mark of the support body as the depressions originating from the other edge after a rotation of the support body by 180° about its transverse axis.

This ensures that the pockets are always in the same position during filling, i.e. independent of whether the one or the other edge of the support body faces the adhesive agent filling device.

To ensure that the adhesive agent does not flow through and exit the gap between the blank and the support body before curing, a characteristic feature that also is to be emphasized intends that from the inner surface, i.e. from the wall of the support body, project baffles that inhibit the free flow of the adhesive agent. The baffles hereby so to speak provide the option of an adhesive reservoir. In this respect, it is in particular intended that the structure in a supplementary or alternative manner is formed by at least one elevation such as a ridge and/or depression originating from the wall, whereby preferably the elevation and/or depression extending at some distance from the edge is provided in addition to the at least one preferably pocket-shaped depression.

In particular it may be intended in this connection that in the central area of the inner circumferential surface extends a preferably circumferential ridge or depression such as a groove, which in particular extends in parallel to the edges.

To arrange the blank in the support body with an equidistant distance to the circumferential surface it may further be intended that one or several projections originate from the inner circumferential surface, such as for example ridges that at least in sections extend with a height higher than that of the inner circumferential surface and serve as support for the blank.

Materials that are preferred for the manufacture of the ring-shaped or hollow-cylindrical support body are fiber reinforced materials such as glass fiber reinforced plastics such as thermoplastics, whereby the thermal expansion coefficient $WAK_H$ of the material of the support body should be matched to the thermal expansion coefficient $WAK_R$ of the blank, in particular so that the WAKs differ no more than 20%, preferably not more than 10%.

The content of fiber, such as glass fiber, of the plastic such as thermoplastic should be between 30% by volume and 70% by volume, in particular approximately 50% by volume.

In particular the support body 10 consists of polyarylamide with a glass fiber content of between 30% by volume and 70% by volume, in particular 50% by volume.

Further details, advantages, and distinguishing features of the invention are not only found in the claims, the characteristic features described therein—individually and/or in combination—, but also in the following description of a preferred embodiment example.

The figures show a support body 10 with a wall 11 of ring-shaped or hollow-cylindrical geometry that surrounds a receiving opening 13 to accommodate a blank 12, which in particular consists of ceramic and possesses a disk-shaped or hollow-cylindrical geometry, as is shown in FIG. 4. In this, the support body 10 surrounds the blank 12 circumferentially, i.e. the inner geometry of the support body 10 should match the circumferential geometry of the blank 12, if necessary with a required undersize of the blank 12.

The support body 10 is required to be able to process the blank 12, which for example may be a zirconium oxide blank, in a processing machine such as a milling machine, to produce for example a dental restoration.

The blank 12 is fixed in position within the support body 10 by means of an adhesive agent, in particular a UV curing adhesive. For this it is necessary to introduce the UV curing adhesive into the gap between the blank 12 and the support body 10. Capillary action draws the adhesive into the gap between the blank 12 and the support body 10. However, introducing the adhesive into the gap is not problem-free.

In order to facilitate this and still to maintain the stability of the support body 10, i.e. without weakening the thickness of the wall 11 of the support body 10, but at the same time to be able to introduce sufficient amounts of adhesive easily even in the case of narrow distances between the inner circumferential surface 14 of the wall 11—hereinafter simply referred to as inner surface—and the outer surface 16 of the blank, the invention's teaching provides for a pattern of pocket-shaped depressions in the inner circumferential surface 14, i.e. the wall 11 of the support body 10, which as an example are marked with the reference labels 18, 20, 22, 24. In this, the pocket-shaped depressions 18, 20, 22, 24, which hereinafter will be referred to as pockets, originate directly at the respective edge, i.e. from the upper edge 26 and the lower edge 28 in the drawing. In this respect the drawing is self-explanatory. The pockets 18, 20, 22, 24 possess first surfaces 30, 32, 34, 36 that extend along the inner circumferential surface 14 and obliquely thereto, which results in a ramp-shaped geometry. The angle α between the respective first surfaces 30, 32, 34, 36 and the inner circumferential surface 14 may be between 20° and 30°, and in particular may be 25° (as is illustrated in FIG. 3B). The first surfaces 30, 32, 34, 36 are bordered by lateral surfaces—two of which have been marked with the reference labels 38, 40 as an example—, which with the first surfaces 30, 32, 34, 36 enclose an obtuse angle, as is illustrated in the top view of FIG. 2. Both in a top view and in a sectional view the respective first surface 30, 32, 34, 36 and the lateral surfaces 38, 40 generate a trapezoidal geometry, as is made evident in the top view of FIG. 2, without this constituting any limitation on the invention's teaching.

However, the support body 10 not only exhibits a trapezoid geometry in a top sectional view but also in a front view, i.e. in a view from the interior of the support body 10 in the direction towards the inner circumferential surface 14, as is shown in FIG. 3A. In other words: The first surface 30, 32, 34, 36 possesses a trapezoidal shape.

The perspective representation of FIG. 1 further illustrates that the pockets 18, 20 originating from the upper edge 26 are offset in such a way from the pockets 22, 24 originating from the lower edge 28 that the pockets originating form one edge are situated in the spaces between the pockets originating from the other edge and vice versa. In this, the pockets 18, 20, 22, 24 are arranged in a way so that after a rotation of the arrangement 10, the pockets that have moved to the top have assumed the exact same positions relative to a reference mark, which in the embodiment example is embodied in form of a longitudinal groove 42, so that filling of adhesive material can always take place at the same positions and thus can easily be automated.

In other words: If the support body 10 is rotated by the reference mark amount, then positions of the pockets 18, 20 which in the drawing are now at the top, will have been occupied by pockets that in the graphic representation originate from the lower edge 28.

The figures further illustrate that longitudinal ridges originate from the inner surface 14, in particular from the lower pockets 22, 24 in the present embodiment example. A corresponding ridge is labeled with the reference label 44 as an example (FIG. 5). This ridge 44, which extends in parallel to the longitudinal axis of the support body 10, protrudes into the interior of the support body 10 to such an extent that a blank 12 accommodated in the support body 10 is positioned relative to the inner surface 14 in a way so that one obtains a gap width between the blank 12 and the support body 10 that is constant along the entire circumference.

. If the length of each pocket 18, 20, 22, 24 along the circumferential direction is A2, then the distance A1 between consecutive pockets 18, 20, 22, 24 should be greater than that. This distance is labeled A1 in FIG. 2. In particular, the distance A1 between successive depressions 18, 20, 22, 24, i.e. in the area of the lowest wall thickness, with respect to the length A2 of the respective depression along the circumferential direction should obey $A2 \leq A1 \leq 2A2$.

With respect to the wall thickness of the wall 11 at the origin of the pockets 18, 20, 22, 24, i.e. at the edge 26, 28, and with respect to the wall thickness of the wall 11 outside of the pockets 18, 20, 22, 24 it should be noted that they should obey proportions such as $8*D1 \geq D2 \geq 2*D1$, whereby D1 is the wall thickness in the area of the origin of the pockets 18, 20, 22, 24 and D2 represents the wall thickness outside of the pockets 18, 20, 22, 24.

To mention specific figures; the wall thickness D2 can for example be 1.5 mm to 5.0 mm, in particular 2.5 mm and the wall thickness in the pocket 18, 20, 22, 24 entrance area can be for example 0.5 mm to 0.9 mm, in particular 0.7 mm.

The height of the holding bracket 10 may for example be between 5 mm and 30 mm, in particular in dependence of the height of the blank to be accommodated, which preferably possesses an extent of its height that is greater than that of the support body 10, i.e. its circular outer surfaces 44, 46 project beyond the edges 26, 28.

The inner diameter of the holding bracket 10 may for example be 94 mm to 100 m, to provide some exemplary figures.

Between the edges 26, 28, which extend parallel relative to each other, in the central area of the support body 10 and in particular originating from the inner surface 14, extends a preferably circumferential ridge 43 (FIG. 1, 5), which prevents the adhesive agent flowing through the gap between the blank 12 and the support body 10 from dripping out on the opposite side. Rather, the corresponding ridge 43 in this respect acts as a baffle. Other geometries for the retention of the adhesive agent are of course also possible. The ridge 43 is forming a structure.

Feasible materials for the support body 10 are in particularly fiber reinforced such as glass fiber reinforced plastics such as thermoplastics, whereby the thermal expansion coefficient $WAK_H$ of the material of the support body 10 should be matched to the thermal expansion coefficient $WAK_R$ of the blank 12; in particular the WAKs should differ no more than 20%, preferably no more than 10%. The fiber content, such as glass fiber content, of the plastic, such as thermoplastic, should be between 30% by volume and 70% by volume, in particular approximately 50% by volume.

In particular, the support body 10 consists of polyarylamide with a glass fiber content of 30% by volume to 70% by volume, in particular 50% by volume.

Irrespective hereof, the figures are self-explanatory and illustrate the characteristic features of the support body 10 of the invention unambiguously.

The invention claimed is:

1. A support body for a blank comprising: a receiving opening for the blank that is surrounded by an inner circumferential surface bordered by an upper and a lower edge and when the blank is fixed in position within the support body, the blank is bonded to the support body by means of an adhesive agent, whereby the support body includes a hollow cylindrical geometry and circumferentially surrounds the blank, wherein the inner circumferential surface includes a structure in form of a plurality of depressions that extends to at least one of the upper and lower edges, at least one elevation, or both to accommodate the adhesive agent; wherein the plurality of depressions is formed within a thickness of a wall of the support body that is bordered by the inner circumferential surface, wherein the plurality of depressions are bordered by a first surface extending along the inner circumferential surface and between lateral surfaces extending perpendicularly to the inner circumferential surface, wherein an angle $\alpha$ is defined between the first surface of the plurality of depressions and the inner circumferential surface to be between $20° \leq \alpha \leq 30°$, wherein in an area of at least one of the plurality of depressions, the wall of the support body in an edge area possesses a thickness D1 and the wall outside of at least one of the plurality of depressions possesses a thickness D2, whereby $8*D1 \geq D2 \geq 2*D1$;

wherein in a central area of the inner circumferential surface extends a circumferential ridge, which extends in parallel to at least one of the upper and lower edges to prevent the adhesive agent flowing through a gap between blank and support body from dripping out on an opposite side; and wherein from the inner circumferential surface originate one or several projections such that sections of the one or several projections extend above or below the circumferential ridge to serve as support for the blank.

2. The support body of claim 1, wherein the plurality of depressions include a plurality of pocket-shaped depressions within the thickness of the wall of the support body that is bordered by the inner circumferential surface.

3. The support body of claim 1, wherein the plurality of depressions originate from a receiving-side area of both the upper and the lower edge, and which terminate at some distance from the center of the inner circumferential surface.

4. The support body of claim 1, wherein a distance from the first surface to a central axis of the support body decreases from one edge along the direction towards an opposite edge.

5. The support body of claim 1, wherein the plurality of depressions are uniformly distributed along the inner circumference of the support body.

6. The support body of claim 1, wherein the plurality of depressions originating from the upper edge of the at least one edge will exhibit the same distances to a reference mark of the support body as the plurality of depressions originating from the lower edge of the at least one edge after a rotation of the support body by 180° about its transverse axis.

7. The support body of claim 1, wherein the structure is formed by at least one elevation, at least one depression, or both that extends at some distance to the at least one of the upper and lower edges and originates from the inner circumferential surface of the wall.

8. The support body of claim 7, wherein the at least one elevation, the at least one depression, or both extending at some distance to the at least one of the upper and lower edge is provided in addition to a plurality of pocket-shaped depressions of the plurality of depressions.

9. The support body of claim 1, wherein a distance A1 between successive depressions and a length A2 of one of the successive depressions along the circumferential direction obeys $A2 \leq A1 \leq 2*A2$.

10. The support body of claim 1, wherein the support body includes a material that includes plastic, wherein the thermal expansion coefficient $WAK_H$ of the material is matched to the thermal expansion coefficient $WAK_R$ of the blank, and wherein the thermal expansion coefficients differ no more than 20%.

11. The support body of claim 1, wherein the support body includes a material that includes plastic, wherein the thermal expansion coefficient $WAK_H$ of the material is matched to the thermal expansion coefficient $WAK_R$ of the blank, and wherein the thermal expansion coefficients differ no more than 10%.

12. The support body of claim 11, wherein the plastic is a fiber reinforced plastic.

13. The support body of claim 12, wherein the fiber reinforced plastic is a glass fiber reinforced plastic.

14. The support body of claim 13, wherein the glass fiber reinforced plastic is a thermoplastic.

15. The support body of claim 13, wherein the fiber content of the support body amounts to between 30% by volume and 70% by volume.

* * * * *